United States Patent [19]

Haas et al.

[11] Patent Number: 4,546,121

[45] Date of Patent: Oct. 8, 1985

[54] USE OF POLYHYDROXYALKYL MONOUREAS FOR POLYURETHANE FOAMS, DISPERSIONS OF THE POLYHYDROXYALKYL MONOUREAS IN POLYOLS AND NEW TRIS-HYDROXYALKYL MONOUREAS

[75] Inventors: Peter Haas, Haan; Geza Avar; Hartwig Grammes, both of Leverkusen, all of Fed. Rep. of Germany

[73] Assignee: Bayer Aktiengesellschaft, Leverkusen, Fed. Rep. of Germany

[21] Appl. No.: 645,204

[22] Filed: Aug. 29, 1984

[30] Foreign Application Priority Data

Sep. 10, 1983 [DE] Fed. Rep. of Germany ....... 3332794

[51] Int. Cl.[4] .............................................. C08G 18/14
[52] U.S. Cl. .................................... 521/164; 252/182; 252/357; 252/609; 521/167; 564/60
[58] Field of Search ................. 521/164, 167; 252/182, 252/357, 609; 564/60

[56] References Cited

U.S. PATENT DOCUMENTS

| | | | |
|---|---|---|---|
| 3,277,027 | 10/1966 | Hennig et al. | 564/60 |
| 3,519,680 | 7/1970 | Wismer et al. | 260/482 |
| 3,560,564 | 2/1971 | Trevel et al. | 564/60 |
| 4,180,631 | 12/1979 | Yukuta et al. | 521/164 |
| 4,246,361 | 1/1981 | Yukuta et al. | 521/167 |

FOREIGN PATENT DOCUMENTS

| | | |
|---|---|---|
| 1369677 | 9/1963 | France . |
| 2360619 | 3/1978 | France . |
| 2381077 | 9/1978 | France . |
| 1127605 | 9/1968 | United Kingdom . |
| 1223320 | 2/1971 | United Kingdom . |

*Primary Examiner*—Maurice J. Welsh

*Attorney, Agent, or Firm*—Gene Harsh; Joseph C. Gil

[57] ABSTRACT

This invention relates to the use of mono- to tetrahydroxyalkyl monoureas corresponding to the following general formula

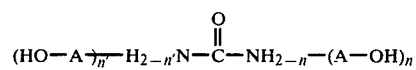

in which A represents a $C_2$–$C_6$-alkylene group optionally containing OH-groups, $n = 0$, 1 or 2.

$n' = 1$ or 2 and $n + n' = 1$, 2, 3 or 4, preferably 2–4 and, more preferably, 3, as reactive flameproofing agents in quantities of from 3 to 100 parts by weight and preferably in quantities of from 11.5 to 50 parts by weight, based on 100 parts by weight of relatively high molecular weight compounds having molecular weights of from 400 to 10,000, preferably relatively high molecular weight polyols, for the production of flameproofed polyurethane foams, and preferably integral skin foams or semirigid to rigid foams. The invention also relates to dispersions or suspensions of mono- to tetrapolyhydroxyalkyl monoureas corresponding to the above formula in relatively high molecular weight compounds containing terminal hydroxyl, primary or secondary amino, carboxyl or hydrazide groups. Preferred are relatively high molecular weight polyols, having a molecular weight in the range from 400 to 10,000. The content of polyhydroxyalkyl monoureas amounts to between 3 and 50% by weight. Finally, the invention relates to tris-hydroxyalkyl monoureas corresponding to the above formula in which $n = 2$, $n' = 1$ and the sum of $n + n' = 3$.

15 Claims, No Drawings

USE OF POLYHYDROXYALKYL MONOUREAS FOR POLYURETHANE FOAMS, DISPERSIONS OF THE POLYHYDROXYALKYL MONOUREAS IN POLYOLS AND NEW TRIS-HYDROXYALKYL MONOUREAS

BACKGROUND OF THE INVENTION

When using polyurethane foams, a high degree of flame resistance is important in certain applications. This degree of flame resistance can be expressed in Standards on inflammability which can and do differ from one another depending upon the particular application envisaged, and which are often aimed at specific end uses. Standards which may be regarded in this light are the MVSS-302-Test, the Bundesbahn Test, the Lufthansa Test (FAR 25,853) and the small burner test according to DIN 53438. Much has been written on this subject of flame resistance.

Commercially, the esters of phosphorus-containing acids and derivatives thereof are used in polyurethane foams. The compounds in question include trischloroethyl phosphate (and higher homologs thereof), tricresyl phosphate, derivatives of aminomethyl phosphonic acid esters and tris-(2,3-dibromopropyl)-phosphate. Bromine-containing butene and butane diols and their relatively high molecular weight oxirane adducts, melamine and its phosphonic acid derivatives are also known flameproofing additives.

Unfortunately, the use of the above-mentioned flameproofing agents involves disadvantages for several reasons. In addition to the adverse physiological effects of $\beta$-halogen esters of phosphorus, the inadequate stability to hydrolysis of compounds of this class is a serious disadvantage. This is particularly unpleasant to the compounder of the polyurethane starting components, because the addition reaction is of course known to be catalyzed by compounds containing tertiary amino groups. Due to this instability of the flameproofing agents used (which is even worse in the basic range) formulations of the starting materials show only limited storage stability. Changes in activity lasting several hours are even observed in formulations freshly prepared just before processing. In general, they can only be corrected with considerable difficulty, the parts affected being regarded as waste because post-catalysis involves many problems.

Additionally, conventional flameproofing agents also have a plasticizer effect which is reflected in a considerable reduction in the thermal stability of the foam under load. In addition, conventional flameproofing agents undergo a gradual loss of activity through the volatility of the compounds used. In automobiles, for example, this diffusability is reflected in the form of recurring deposits on glass surfaces such as windshields (fogging).

The object of the present invention is to provide reactive flameproofing compounds for polyurethane foams which do not have any of the disadvantages of the prior art, namely
 inadequate dispersibility or miscibility;
 inadequate stability in storage of the mixture of starting materials containing flameproofing agents;
 plasticizing effects of the flameproofing agent;
 poor thermal stability of the foam under load caused by the additives;
 diffusion effects and exudation of the flameproofing agent, i.e. a reduction in activity; and
 emission of hydrohalides in the event of fire.

DESCRIPTION OF THE INVENTION

Surprisingly, mono- to tetrahydroxyalkyl monoureas corresponding to the following general formula

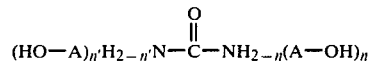

in which

A represents linear or branched, $C_2$–$C_6$-alkylene groups optionally containing one or more OH-groups (provided that the total number of hydroxyl groups in the urea does not exceed five), and preferably is selected from ethylene groups, 1,2- and/or 1,3-propylene groups and, most preferably, ethylene groups and/or 1,2-propylene groups; preferably the total number of hydroxyl groups in the urea does not exceed four;
 $n=0$, 1 or 2;
 $n'=1$ or 2; and,
 $n+n'=1$, 2, 3 or 4,
are outstandingly effective, reactive flameproofing agents in polyurethane foams. Accordingly, they may be used, preferably in the form of dispersions or suspensions in relatively high molecular weight compounds containing NCO-reactive groups, preferably relatively high molecular weight polyols, for the production of polyurethane foams.

Many mono-, bis- and tetrahydroxy alkyl monoureas are known. They are normally synthesized by reacting urea and the corresponding amines, as already described, for example, in U.S. Pat. No. 3,560,564, in German Pat. No. 1,468,398, in British Pat. No. 1,127,605 or in German Offenlegungsschrift No. 27 03 185. The trishydroxyalkyl monoureas which may be used particularly favorably as flameproofing agents are generally liquids which form stable dispersions in the polyols at room temperature. They have not been described in the literature and, accordingly, are believed to be new compounds.

The present invention also relates to the dispersions or suspensions of mono-, bis-, tris- or tetrahydroxyalkyl monoureas in relatively high molecular weight compounds containing terminal hydroxyl, primary or secondary amino, carboxyl or hydrazide groups. It is preferred to use relatively high molecular weight polyols and, more preferably, more than difunctional polyethers, having molecular weights in the range from 400 to 10,000. They are used in amounts of from 3 to 50% by weight and preferably from 10 to 30% by weight of the monoureas in the relatively high molecular weight compounds. Dispersions of tris-hydroxyalkyl monoureas in relatively high molecular weight, more than difunctional polyethers are particularly preferred.

Some of the urea derivatives have already been used as reaction component in polyurethane plastics, as described, for example, in German Pat. Nos. 933,783 and 959,679. In those cases, however, they are used solely as chain extending agents in polyurethane polyester elastomers. The monoureas used include monoureas of the above general formula in which A=ethylene, $n=1$, $n'=1$ and A=ethylene, $n=0$ and $n'=2$, which have a processing temperature in the range from 100° to 130° C. However, these ureas have the considerable disadvantage that they solidify in crystalline form after prolonged standing. Their melting points are of the order of, and above, 100° C. Accordingly, such ureas in question are unsuitable for processing at room temperature, as required in foam technology. Thus n+n'=1 or 2 (symmetrically) are less effective in some cases.

The liquid tris-hydroxyalkyl monourea derivatives (n=2, n'=1) have not been described and are outstanding in their processibility and dispersibility in polyols at room temperature for the production of polyurethane foams and in their effect as flameproofing agents. They may be produced by (a) reacting urea with a mixture of the amines HN(A—OH)$_2$ and H$_2$NA—OH or, in stages, (b) from $NH_2-\underset{\underset{O}{\|}}{C}-NHAOH$ and $HN(A-OH)_2$ (preferred procedure)

or (c) from $NH_2-\underset{\underset{O}{\|}}{C}-N(A-OH)_2$ and $H_2NAOH$;

(preferred procedure)

where A may have the meaning already defined.

The following are examples of useful hydroxyalkyl ureas according to the present invention:

| Structure | Preference |
|---|---|
| HO—CH$_2$—CH$_2$—NH—C(=O)—NH$_2$ | less preferred |
| HO—CH$_2$—CH$_2$—NH—C(=O)—NH—CH$_2$—CH$_2$—OH | less preferred |
| (HO—CH$_2$—CH$_2$)$_2$N—C(=O)—NH$_2$ | less preferred |
| (HO—CH$_2$—CH$_2$)$_2$N—C(=O)—N(CH$_2$—CH$_2$—OH)$_2$ | preferred |
| HO—CH$_2$—CH$_2$—CH$_2$—NH—C(=O)—NH$_2$ | less preferred |
| HO—CH(CH$_3$)—CH$_2$—NH—C(=O)—NH$_2$ | less preferred |
| HO—CH$_2$—CH$_2$—NH—C(=O)—NH—CH$_2$—CH$_2$—CH$_2$—OH | preferred |
| HO—CH$_2$—CH$_2$—CH$_2$—NH—C(=O)—NH—CH$_2$—CH$_2$—CH$_2$—OH | less preferred |
| HO—CH(CH$_3$)—CH$_2$—NH—C(=O)—NH—CH$_2$—CH$_2$—OH | preferred |
| (HO—CH$_2$—CH$_2$)$_2$N—C(=O)—NH—CH$_2$—CH$_2$—OH | particularly preferred |
| (HO—CH$_2$—CH$_2$)$_2$N—C(=O)—NH—CH$_2$—CH(CH$_3$)—OH | particularly preferred |
| (HO—CH$_2$—CH$_2$)$_2$N—C(=O)—NH—CH$_2$—CH$_2$—CH$_2$—OH | particularly preferred |
| (HO—CH$_2$—CH$_2$—CH$_2$)$_2$N—C(=O)—NH—CH$_2$—CH$_2$—CH$_2$—OH | particularly preferred |
| (HO—CH$_2$—CH$_2$—CH$_2$)$_2$N—C(=O)—N(CH$_2$—CH$_2$—CH$_2$—OH)$_2$ | preferred |
| (HO—CH$_2$—CH$_2$—CH$_2$)$_2$N—C(=O)—NH—CH$_2$—CH$_2$—OH | particularly preferred |
| (HO—CH$_2$—CH$_2$—CH$_2$)$_2$N—C(=O)—NH—CH$_2$—CH(CH$_3$)—OH | particularly preferred | poses limits upon the processibility of both symmetrical and asymmetrical bis(hydroxyethyl)ureas.

The products (of which the liquid types are particularly preferred for problem free processing) are used in quantities of from 3 to 100 parts, preferably in quantities of from 11.5 to 50 parts and, most preferably, in quantities of from 11.5 to 30 parts, based on 100 parts of the relatively high molecular weight compounds containing at least 2 isocyanate-reactive hydrogen atoms. Preferred isocyanate-reactive compounds are relatively high molecular weight polyols, having molecular weights in the range from 400 to 10,000. Preferred dispersions contain 3 to 50% by weight of the monoureas in the relatively high molecular weight compound. Although mixtures of mono- to tetra-hydroxyalkyl monoureas may be used, mixtures in which at least one component (and particularly at least 50%) consists of tris-hydroxyalkyl monoureas are particularly preferred. Dispersions of the tris-hydroxyalkyl monoureas, particularly in more than difunctional polyethers, are most particularly preferred.

Foam-forming starting materials used for the production of polyurethane foams using the flameproofing agents according to the invention include those known in the art including isocyanate reactive compounds, isocyanates and auxiliaries.

Compounds containing at least two isocyanate-reactive hydrogen atoms and having a molecular weight of generally from 400 to 10,000 are generally used to produce polyurethane foams. In addition to compounds containing amino groups, thiol groups or carboxyl groups, compounds of this type are, preferably, compounds containing hydroxyl groups and, more preferably, compounds containing from 2 to 8 hydroxyl groups, especially those having a molecular weight in the range from 600 to 6000 and preferably in the range from 1500 to 4000. Suitable hydroxyl functional materials include polyesters, polyethers, polythioethers, polyacetals, polycarbonates and polyester amides containing from 2 to 4 hydroxyl groups of the type known for the production of homogeneous and cellular polyurethanes and described, for example, in German Auslegeschrift No. 28 32 253, pages 11 to 18. Particularly preferred are polyethers of the type obtained by the addition of one or more alkylene oxides (ethylene oxide and especially propylene oxide) to difunctional or higher "starters" (e.g., propylene, glycol, glycerol, sorbitol, formose, triethanolamine and trimethylol propane). Also useful are polyethers containing polyadducts of diisocyanates and hydrazine and/or diamines and/or glycols or polymers and/or graft polymers, preferably of styrene and acrylonitrile, in dispersed or dissolved form. The preferred polyethers have an average functionality of more than 2.0.

Compounds containing at least two isocyanate-reactive hydrogen atoms and having a molecular weight of from 18 to 399 can also be used as starting materials. In this case, too, the compounds in question include compounds containing hydroxyl groups and/or amino groups and/or thiol groups and/or carboxyl groups and/or hydrazide groups. Preferred are compounds containing hydroxyl groups and/or amino groups which serve as chain-extending agents or crosslinking agents. These compounds generally contain from 2 to 8 and preferably from 2 to 4 isocyanate-reactive hydrogen atoms. Examples of these compounds can be found in German Auslegeschrift No. 28 32 253, pages 19 to 20 and include water, hydrazine, ethylene glycol, 1,4-butane diol, trimethylol propane, formitol mixtures or adipic acid dihydrazide.

Aliphatic, cycloaliphatic, araliphatic, heterocyclic and, in particular, aromatic polyisocyanates of the type described, for example by W. Siefken in Justus Liebigs Annalen der Chemie, 562, pages 75 to 136 can also be used. Examples include those corresponding to the formula $Q(NCO)_n$, in which $n=2$ to 4 (preferably 2) and Q represents an aliphatic hydrocarbon radical containing from 2 to 18 (and preferably from 6 to 12 carbon atoms), a cycloaliphatic hydrocarbon radical containing from 4 to 20 (and preferably from 5 to 11 carbon atoms), an aromatic hydrocarbon radical containing from 6 to 20 (and preferably from 6 to 13 carbon atoms) or an araliphatic hydrocarbon radical containing from 8 to 15 (and preferably from 8 to 13 carbon atoms). Examples of such polyisocyanates are described in German Auslegeschrift No. 28 32 253, pages 10 to 11. Particularly preferred are the commercially available polyisocyanates, for example 2,4- and/or 2,6-tolylene diisocyanate and mixtures of these isomers ("TDI"); diphenyl methane diisocyanates (4,4'- and/or 2,4'- and/or 2,2'-isomer); polyphenyl polymethylene polyisocyanates of the type obtained by phosgenating aniline-formaldehyde condensates ("crude MDI") and "modified polyisocyanates" which contain, for example, carbodiimide groups, urethane groups, allophanate groups, isocyanurate groups, urea groups and/or biuret groups. Particularly preferred modified polyisocyanates are those derived from 2,4- and/or 2,6-tolylene diisocyanate and preferably from 4,4'- and/or 2,4'-diphenyl methane diisocyanate. If only difunctional, relatively high molecular weight compounds (and, optionally, other only difunctional, low molecular weight chain extending agents) are used, it is preferred to use modified polyisocyanates having a functionality of more than 2.0, i.e. tri- and/or higher polyisocyanates.

Auxiliaries and additives, such as readily volatile inorganic, and preferably organic substances acting as blowing agents; catalysts such as tertiary amines, tin-(II) and tin-(IV) compounds; surface-active additives, such as emulsifiers and foam stabilizers; reaction retarders, for example acid-reacting substances, such as hydrochloric acid or organic acid halides; cell regulators such as paraffins, fatty alcohols or dimethyl polysiloxanes; pigments or dyes; stabilizers against the effects of ageing, light and weather; plasticizers, fungistatic and bacteriostatic agents; and fillers, are optionally added. These optional auxiliaries and additives are known and are described in detail, for example in German Auslegeschrift No. 2,732,292, pages 21 to 24. Further examples of the auxiliaries and additives in question can be found in Kunststoff Handbuch, Vol. VII, published by Vieweg and Hochtlen, Carl-Hanser-Verlag, Munich, 1966, pages 103 to 113.

The reactive mono- to tetrahydroxyalkyl monoureas and preferably the tris-hydroxyalkyl ureas are normally mixed with the relatively high molecular weight (preferably polyol) compound in the quantities indicated. Fine suspensions of solid compounds in the relatively high molecular weight polyols or polyhydroxyl compounds preferably dispersed in liquid form are formed. The polyhydroxyalkyl ureas are optionally dispersed in the relatively high molecular weight polyols at temperatures above their melting point. In addition, the mixture may contain the auxiliaries and additives normally used in the production of foams. The mixture of starting

| | |
|---|---|
| [HO—CH(CH₃)—CH₂]₂N—C(=O)—NH—CH₂—CH(CH₃)—OH | particularly preferred |
| [HO—CH(CH₃)—CH₂]₂N—C(=O)—NH—CH₂—CH₂—CH₂—OH | particularly preferred |
| [HO—CH(CH₃)—CH₂]₂N—C(=O)—NH—CH₂—CH₂—OH | particularly preferred |
| [HO—CH₂—CH(OH)—CH₂]₂N—C(=O)—NH—CH₂—CH₂—OH | particularly preferred |
| [HO—CH₂—CH(OH)—CH₂]₂N—C(=O)—NH—CH₂—CH(OH)—CH₂—OH | particularly preferred |
| (HO—CH₂—CH₂)₂N—C(=O)—NH—CH₂—CH(OH)—CH₂—OH | particularly preferred |
| (HO—CH₂—CH₂)₂N—C(=O)—NH—CH₂—CH₂—CH(OH)—CH₃ | particularly preferred |
| (HO—CH₂—CH₂)₂N—C(=O)—NH—C(CH₃)(CH₂OH)—CH₂—OH | particularly preferred |
| HO—CH₂—CH₂—NH—C(=O)—NH—C(CH₃)(CH₂OH)—CH₂—OH | less preferred |
| NH₂—C(=O)—NH—C(CH₃)(CH₂OH)—CH₂—OH | less preferred |
| NH₂—C(=O)—NH—C(CH₂OH)₃ | less preferred |
| HO—CH₂—CH₂—NH—C(=O)—NH—C(CH₂OH)₃ | less preferred |
| (HO—CH₂—CH₂)₂N—C(=O)—NH—C(CH₂OH)₃ | less preferred |

The hydroxyalkyl ureas in which A=ethylene may be placed in the following order according to their flameproofing activity:

HO—CH₂—CH₂—NH—C(=O)—NH₂ <

HO—CH₂—CH₂—NH—C(=O)—NH—CH₂—CH₂—OH <

(HO—CH₂—CH₂)₂N—C(=O)—N(CH₂—CH₂—OH)₂ <

(HO—CH₂—CH₂)₂N—C(=O)—NH₂ <

(HO—CH₂—CH₂)₂N—C(=O)—NH—CH₂—CH₂—OH.

In this connection, it is surprising that tris-hydroxyethyl urea produces the best flameproofing results and that tetrahydroxyethyl urea has a poorer flameproofing effect. This does not of course take into account the crystallization behavior of the products mentioned. As already mentioned, such crystallization behavior imin a water jet vacuum at 80° C.; yield quantitative. The product remains liquid; viscosity: 3300 mPas (25° C.).

Analysis calculated: C 46.5, H 8.7, N 13.6; observed: C 46.2, H 8.7, N 14.7.

$$(HO-CH_2-CH_2)_2N-\overset{\overset{O}{\|}}{C}-NH-(CH_2)_3-OH \qquad 8.$$
$$C_8H_{18}N_2O_4\ (206)$$

From 148 g (1 mole) of N,N-bis-2-hydroxyethyl urea according to Example 1 and 75 g (1 mole) of 3-amino-1-propanol by heating to 100°–140° C. and aftertreatment in a water jet vacuum at 80° C.; yield quantitative. The urea remains liquid; viscosity: 4600 mPas (25° C.).

$$[HO-\overset{\overset{CH_3}{|}}{CH}-CH_2]_2N-\overset{\overset{O}{\|}}{C}-NH-(CH_2)_2-OH \qquad 9.$$
$$C_9H_{20}N_2O_4\ (210)$$

From 176 g (1 mole) of N,N-bis-2-hydroxypropyl urea according to Example 6 and 61 g of ethanolamine by elimination of ammonia at 120° to 140° C. and aftertreatment in a water jet vacuum at 80° C.; yield quantitative. OH number 770, calculated 763.

$$(HO-CH_2-CH_2)_2-N-\overset{\overset{O}{\|}}{C}-NH-CH_2-\overset{\overset{OH}{|}}{CH}-CH_3 \qquad 10.$$
$$C_8H_{20}N_2O_4\ (220)$$

From 148 g (1 mole) of N,N-bis-2-hydroxyethyl urea according to Example 1 and 89 g (1 mole) of 4-amino-2-butanol at 120° to 140° C. and aftertreatment in a water jet vacuum at 80° C.; yield quantitative. OH number 780, calculated 763.

$$(HO-CH_2-CH_2)_2N-\overset{\overset{O}{\|}}{C}-NH-\underset{\underset{CH_3}{|}}{\overset{\overset{CH_2-OH}{|}}{C}}-CH_2-OH \qquad 11.$$
$$C_9H_{20}N_2O_5\ (236)$$

From 148 g (1 mole) of N,N-bis-2-hydroxyethyl urea according to Example 1 and 105 g (1 mole) of 2-amino-2-methyl-1,3-propane diol at 120° to 140° C. and aftertreatment in a water jet vacuum at 80° C.; yield quantitative. OH number 900, calculated 950; viscosity: 57000 mPas (25° C.).

Analysis calculated: C 45.7, H 8.4, N 11.9; observed: C 45.4, H 8.3, N 12.3.

$$NH_2-\overset{\overset{O}{\|}}{C}-NH-\underset{\underset{CH_3}{|}}{\overset{\overset{CH_2-OH}{|}}{C}}-CH_2-OH \qquad 12.$$
$$C_5H_{12}N_2O_3\ (148)$$

From 60 g (1 mole) of urea and 105 g (1 mole) of 2-amino-2-methyl-1,3-propane diol at 80° to 120° C. and aftertreatment in a water jet vacuum at 80° C.; yield quantitative; OH number 850, calculated 824.

$$NH_2-\overset{\overset{O}{\|}}{C}-NH-C\underset{\diagdown CH_2-OH}{\overset{\diagup CH_2-OH}{-CH_2-OH}} \qquad 13.$$
$$C_5H_{12}N_2O_4\ (164)$$

From 60 g (1 mole) of urea and 121 g (1 mole) of 2-amino-2-hydroxymethyl-1,3-propane diol at 80° to 120° C. and aftertreatment in a water jet vacuum at 80° C.; yield quantitative; OH number 1040, calculated 1022.

$$(HO-CH_2-CH_2)_2N-\overset{\overset{O}{\|}}{C}-NH-C\underset{\diagdown CH_2-OH}{\overset{\diagup CH_2-OH}{-CH_2-OH}} \qquad 14.$$
$$C_9H_{20}N_2O_6\ (252)$$

From 74 g of N,N-bis-(2-hydroxyethyl)-urea and 61 g of 2-amino-2-hydroxymethyl propane diol at 120° to 140° C. and aftertreatment in a water jet vacuum at 80° C.; yield quantitative; OH number calculated 1110, OH number observed 1150.

$$[HO-\overset{\overset{CH_3}{|}}{CH}-CH_2]_2N-\overset{\overset{O}{\|}}{C}-NH-CH_2-\overset{\overset{CH_3}{|}}{CH}-OH \qquad 15.$$
$$C_{10}H_{22}N_2O_3\ (218)$$

From 528 g (3.0 m) of N,N-bis-2-hydroxypropyl urea according to Example 6 and 225 g (3 m) of 2-amino-propanol by heating to 120°–140° C. and aftertreatment in a water jet vacuum at 80° C.; yield 694 g; viscosity 4500 mPas (25° C.).

Analysis calculated: C 51.2, H 9.4, N 11.95; observed: C 50.7, H 8.5, N 12.4.

(B) Use in the production of integral skin and rigid foams

The individual flameproofing components used are as shown in Table 1. The following basic formulation was used in all the Examples:

The polyol base component of the mixture consisted of:

100 parts by weight of a trifunctional polyether polyol (OH number 35) which had been produced by the alkoxylation of trimethylol propane using propylene oxide and subsequent addition of approximately 15%, based on the total weight of ethylene oxide, 9 parts by weight of ethylene glycol, 0.4 part by weight of diazabicyclooctane (33% in diisopropanol, "33 LV", a product of Houdry/Huls of D 4370 Marl), 14 parts by weight of trichlorofluoromethane.

The polyisocyanate component consisted of the quantity indicated in the Table of a liquid, dipropylene-glycol-modified, substantially difunctional polyisocyanate mixture of the diphenyl methane series having an NCO content of 28% and a viscosity at 25° C. of 130 mPas.

100 parts of the dispersion or suspension of the hydroxyalkyl monoureas in the polyol base component were foamed with the quantities of isocyanate indicated in Table 1.

The polyol base component is stirred with the particular flameproofing components in the quantities indicated in the Table either at room temperature or at elevated temperature. Slightly cloudy dispersions of the hydroxyalkyl ureas in the polyols are obtained and show adequate stability (shelf lives of up to several months). Solid hydroxyalkyl monoureas may also be converted into suspensions in the relatively high molecmaterials remains stable in storage over standard storage periods.

A preferred dispersion comprises from 3 to 50% by weight (preferably 10 to 30% by weight) of the mono- to tetrahydroxyalkyl monoureas in the relatively high molecular weight compounds containing at least 2 NCO-reactive terminal groups (hydroxyl, primary and/or secondary amino, carboxyl or hydrazide groups) and having molecular weights of from 400 to 10,000 (most preferably in relatively high molecular weight polyols).

The main field of application for the flameproofing agents is in the production of integral skin foams and semi-rigid and rigid foams. In this connection, polyurethane foam systems containing water instead of organic blowing agents are preferred, although polyurethane foam systems containing water as blowing agent which optionally lead to elastic foams may also be used. It has surprisingly been found that the flameproofing agents used in accordance with the invention do not have a cell-opening effect in aqueous systems producing elastic, flexible foams, as is described in European Patent No. 68 281 for polyhydroxyalkyl amide derivatives of polybasic carboxylic acids.

The main fields of application for the products obtainable in accordance with the invention are flameproof (particularly semirigid or rigid) polyurethane foams which may be used, for example, in the field of transportation. Rigid foams for insulation purposes and flameproof integral skin foams for moldings of the type used, for example, in the automotive industry are also preferred fields of use.

The particular suitability of the polyurethane foams flameproofed with the mono- to tetrahydroxyalkyl monoureas according to the invention for the interior parts of vehicles of all kinds is established by special test methods, namely the MVSS 302 Test, the Bundesbahn Test and the Lufthansa Test (FAR 25,853). These tests are discussed in detail in the Examples which follow.

As the results of the fire tests show, the flameproofing agents according to the invention are extremely effective in polyurethane foams, even when used on their own. However, they may also be used in combination with standard flameproofing agents.

The invention is further illustrated, but is not intended to be limited by the following examples in which all parts and percentages are by weight unless otherwise specified.

EXAMPLES

Experimental Part (A) Production of the hydroxyalkyl monoureas

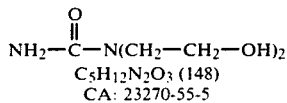
1.

From 600 g (10 moles) of urea and 1050 g (10 moles) of diethanolamine by elimination of ammonia at 100° to 140° C. and aftertreatment in a water jet vacuum at 80° C. The yield was substantially quantitative. The reaction product solidifies in completely crystalline form over different periods; OH number 766, calculated 755. (Treatment for elimination of NH₃ was generally between 600 and 720 minutes; after treatment was about 150–200 minutes, in all examples 1–15).

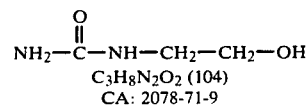
2.

From 600 g (10 moles) of urea and 610 g (10 moles) of ethanolamine by elimination of ammonia at 80° to 120° C. and aftertreatment in a water jet vacuum at 80° C. The yield was substantially quantitative; OH number 550, calculated 538.

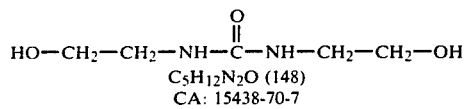
3.

From 600 g (10 moles) of urea and 1220 g (20 moles) of ethanolamine by elimination of the corresponding quantity of ammonia at 80° to 120° C. and aftertreatment in a water jet vacuum at 80° C. The yield was substantially quantitative. The product solidifies after brief standing; OH number 786, calculated 755.

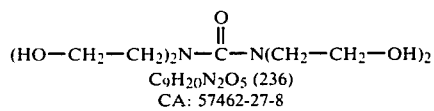
4.

From 600 g (10 moles) of urea and 2100 g (20 moles) of diethanolamine by elimination of ammonia at 100° to 140° C. and aftertreatment in a water jet vacuum at 80° C.; yield 2340 g; OH number 1090, calculated 1050. The product remains liquid; viscosity: 4000 mPas (25° C.).

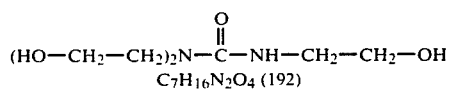
5.

From 3340 g (22.6 moles) of N,N-bis-2-hydroxyethyl urea according to Example 1 and 1380 g (22.6 moles) of ethanolamine by heating to 120°–140° C. and aftertreatment in a water jet vacuum at 80° C.; yield 4200 g; viscosity 4200 mPas at 25° C.; OH number 940, calculated 880.

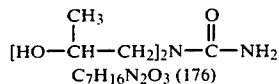
6.

From 150 g (2.5 moles) of urea and 332.5 g (2.5 moles) of diisopropanolamine by heating to 115°–120° C. and aftertreatment in a water jet vacuum at 80° C.; yield substantially quantitative; OH number 640, calculated 636. The product solidifies in wax-like form after brief standing.

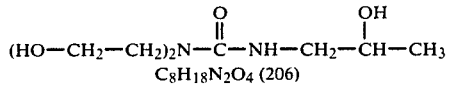
7.

From 148 g (1 mole) of N,N-bis-2-hydroxyethyl urea according to Example 1 and 75 g (1 mole) of 2-aminopropanol by heating to 100°–140° C. and aftertreatment ular weight polyols using high-performance mixing units having a size-reducing effect.

Test specimens: 3 plates measuring 350×100×13 mm measuring marks at 38, 254 and 312 mm

TABLE 1

| Flameproofing Agent (FPA) | Quantity of FPA (parts by wt.) | Polyol base component (parts by wt.) | FPA in parts by wt. per 100 parts by wt. of relatively high molecular weight polyol | Quantity of isocyanate (parts by wt.) | Post-activation with catalyst 33LV |
|---|---|---|---|---|---|
| Tris-(chloroethyl)-phosphate (Comparison) | 10 | 100 | — | 43 | — |
| Compound 2 | 10 | 90 | 11.1 | 52 | — |
| Compound 3 | 15 | 85 | 17.6 | 61 | 1.0 |
| Compound 6 | 10 | 90 | 11.1 | 54 | — |
| Compound 1 | 20 | 80 | 25.0 | 66 | — |
| Compound 4 | 15 | 85 | 17.6 | 70 | 0.4 |
| Compound 5 | 10 | 90 | 11.1 | 60 | — |
| Compound 8 | 20 | 80 | 25.0 | 68 | — |
| Compound 7 | 15 | 85 | 17.6 | 63 | — |
| Compound 15 | 20 | 80 | 25.0 | 65 | — |
| Compound 15 | 15 | 85 | 17.6 | 60 | — |

TABLE 2

Burning behavior after the incorporation of hydroxyalkyl ureas as flameproofing agents in foams having the composition indicated in Table 1.

| Flameproofing agent (FPA) | MVSS 302 classification | FAR 25853 vertical | | | | Bundesbahn Test DV 899/35 | |
|---|---|---|---|---|---|---|---|
| | | length of specimen destroyed (mm) | after flame time (seconds) | drip flame time (seconds) | Passed | degree of flammability | degree of dripability |
| Tris-(chloroethyl)-phosphate (Comparison) | SE | 45 | 32 | 15 | no | B 3 | T 1 |
| FPA 2 | SE | 50 | 11 | 23 | no | B 1 | T 1 |
| FPA 3 | SE | 50 | 11 | 20 | no | B 2 | T 1 |
| FPA 6 | SE | 65 | 18 | 20 | no | B 2 | T 1 |
| FPA 1 | SE | 42 | 0 | 0 | yes | B 3 | T 1 |
| FPA 4 | SE | 33 | 4 | 2 | yes | B 2 | T 1 |
| FPA 5 | SE | 35 | 0 | 0 | yes | B 3 | T 1 |
| FPA 8 | SE | 50 | 3 | 1 | yes | B 3 | T 1 |
| FPA 7 | SE | 40 | 0 | 0 | yes | B 3 | T 1 |
| FPA 15 | SE | 33 | 0 | 0 | yes | B 3 | T 1 |
| FPA 15 | SE | 37 | 0 | 0 | yes | B 3 | T 1 |

The Examples show that, in the FAR 25853 flammability tests in which the length of test specimen destroyed, the afterflame time and the dripflame time are measured, the hydroxyalkyl ureas according to the invention give better results than conventional flameproofing agents.

This is particularly apparent from Examples 1, 5, 8, 7 and 15.

(C) Testing of burning behavior

Almost all flammability tests are based on the risk aspects of certain applications. Accordingly, there are different tests for the various applications, giving results which may not be comparable with one another.

Three fire tests were selected for determining the effectiveness of the flameproofing agents, namely:

(a) procedure for testing the interior trim of motor vehicles according to DIN No. 75 200 which corresponds to the U.S. Federal Motor Vehicle Safety Standards (MVSS) 302

(b) Bundesbahn flammability test (c) burning behavior of aerospace materials: Federal Aviation Regulations (FAR) 25853 (USA).

The dimensions and number of test specimens, the test arrangement, the performance of the test and the requirements to be satisfied are listed in the following schedule:

(a) MVSS 302 (Docket 3—3) (DIN 75 200)

Test arrangement: horizontal
Flame application time: 15 seconds
Determination of the burning rate v between the second and third marks
Requirement: v ≦ 100 mm/min.
Classification: SE (self-extinguishing), SE/NBR (no burning rate, test specimen goes out within 60 seconds), BR (burning, burning rate is indicated).

(b) Bundesbahn Test DV 899/35

Test specimens: 3 plates measuring 300×100×30 mm
Test arrangement: vertical
Flame application time: 3 minutes
Determination of the degree of flammability (% of area burned)
B 4: non-inflammable
B 3: inflammable with difficulty, up to 75% of area burned
B 2: inflammable, 76–90% of area burned
B 1: readily inflammable, 91–100% of area burned
Determination of the degree of dripability
T 4: deforms but does not soften or drip
T 3: deforms seriously, softens or forms strings
T 2: drips without burning
T 1: drips alight and continues burning (c) Lufthansa Test FAR 25 853

Test arrangement: horizontal and vertical
Test specimens horizontal: 3 plates measuring 350×100×13 mm
vertical: 3 plates measuring 350×75×13 mm
Flame application time
    horizontal: 15 seconds
    vertical: 12 seconds
    Requirements
Horizontal: burning rate: 63.4 mm/minute
vertical: char length: 203 mm
afterflame time: 13 seconds
dripflame time: 5 seconds Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for preparing a polyurethane foam by reacting an organic polyisocyanate with relatively high molecular weight compounds which contain isocyanate-reactive hydrogen atoms in the presence of a blowing agent, the improvement wherein a reactive flameproofing agent is included in the reaction mixture in an amount of from 3 to 100 parts per 100 parts of said relatively high molecular weight compound and wherein said flameproofing agent is a mono- to tetrahydroxyalkyl monourea of the following formula:

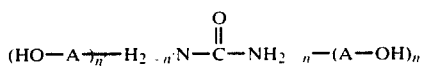

in which

A represents straight-chain or branched $C_2$–$C_6$-alkylene groups which may contain one or more hydroxyl groups provided that the total number of hydroxyl groups in said flameproofing agent does not exceed four,
n = 0, 1 or 2,
n' = 1 or 2 and
n + n' = 1, 2, 3 or 4, with at least 50% by weight of said flameproofing agent coming within the above formula wherein the total number of hydroxyl groups is three wherein n = 2 and wherein n' = 1.

2. The process of claim 1 wherein A is selected from the group consisting of ethylene, 1,2-propylene and 1,3-propylene and n + n' = 2, 3 or 4.

3. The process of claim 1 wherein said amount is from 11.5 to 50 parts by weight.

4. The process of claim 1, characterized in that the mono- to tetrahydroxyalkyl monoureas are used in the form of a dispersion or suspension containing 3 to 50% by weight of said monourea.

5. The process of claim 1 wherein A is an ethylene group and/or 1,2-propylene group.

6. The process of claim 1, characterized in that n + n' = 2, 3 or 4.

7. The process of claim 6, characterized in that said monourea contains three hydroxyl groups.

8. A polyurethane foam produced according to the process of claim 1.

9. A dispersion or suspension comprising from 3 to 50% by weight of a mono-, bis-, tris-, or tetrahydroxyalkyl monourea in a relatively high molecular weight compound containing at least two NCO-reactive terminal groups selected from terminal hydroxyl, primary or secondary amino, carboxyl or hydrazide groups, with the proviso that at least 50% by weight of said monourea is a tris-hydroxyalkyl monourea.

10. The dispersion or suspension of claim 9 wherein said compound is a polyol with a molecular weight of from 400 to 10,000.

11. The dispersion or suspension of claim 10 wherein said monoureas comprise from 10.0 to 30% by weight.

12. The dispersions or suspensions of claim 9, characterized in that said monoureas are bis-, tris- or tetrahydroxyalkyl monoureas.

13. The dispersions or suspensions of claim 12, characterized in that said monourea is a tris-hydroxyalkyl monourea.

14. Tris-hydroxyalkyl monoureas corresponding to the following general formula

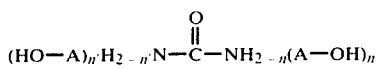

in which

A represents straight-chain or branched $C_2$–$C_6$-alkylene groups which may contain one or more hydroxyl groups provided that the total number of hydroxyl groups in the monourea does not exceed 3,
n = 2 and
n' = 1.

15. The tris-hydroxyalkyl monoureas of claim 14, characterized in that A represents ethylene and/or 1,2-propylene groups.

* * * * *